(12) United States Patent
Nakamura

(10) Patent No.: US 7,136,161 B2
(45) Date of Patent: Nov. 14, 2006

(54) COMPONENT ANALYZING APPARATUS WITH MICROCHIP

(75) Inventor: Shin Nakamura, Moriyama (JP)

(73) Assignee: Shimadzu Corporation, Kyoto (JP)

( * ) Notice: Subject to any disclaimer, the term of this patent is extended or adjusted under 35 U.S.C. 154(b) by 227 days.

(21) Appl. No.: 10/893,221

(22) Filed: Jul. 19, 2004

(65) Prior Publication Data

US 2005/0024636 A1 Feb. 3, 2005

(30) Foreign Application Priority Data

Aug. 1, 2003 (JP) .............................. 2003-284633

(51) Int. Cl.
*G01N 21/64* (2006.01)
*G01N 27/447* (2006.01)

(52) U.S. Cl. ..................... 356/318; 356/417; 356/344

(58) Field of Classification Search ................ 356/317, 356/318, 417, 344
See application file for complete search history.

(56) References Cited

FOREIGN PATENT DOCUMENTS

WO WO 01/53822 A2 * 7/2001

* cited by examiner

*Primary Examiner*—F. L. Evans
(74) *Attorney, Agent, or Firm*—Manabu Kanesaka

(57) ABSTRACT

A component analyzing apparatus includes a microchip having a fine separating flow path for separating components when a sample solution labeled with fluorescence passes therethrough. A light irradiation device is arranged to irradiate light to a predetermined area of the microchip at a predetermined angle so that the proximity field light irradiates at least a portion of the separating flow path of the microchip. A light detecting device is disposed above the microchip to receive the fluorescence discharged from the sample solution labeled with fluorescence present in the separating flow path with the proximity field light generated from light irradiated by the light irradiating device as excitation light.

6 Claims, 5 Drawing Sheets

COMPONENT ANALYZING APPARATUS WITH MICROCHIP

BACKGROUND OF THE INVENTION AND RELATED ART STATEMENT

The present invention relates to a component analyzing apparatus with a microchip suitable for analysis in the field of, mainly, biochemistry, molecular biology and clinical medicine, and especially for analyzing DNA and protein.

A capillary electrophoresis (CE) is a method suitable for separating components having similar structures, such as optical separation and separation of isomers, as well as analyzing bio-components such as peptides, proteins, DNA and sugars. The capillary electrophoresis has been widely used for monitoring clinical medicine, drugs, environment materials or the like. Especially, a microchip type apparatus, i.e. a microchip electrophoresis apparatus, having a micro-flow path using a photo-lithographic technique or the like, is easy to handle and has been widely used for analyzing DNA or the like.

FIGS. 8(a)–8(c) show an example of an electrophoretic chip disclosed in Japanese Patents No. 3077609 and No. 3417344; and FIG. 9 is a perspective view thereof. An electrophoretic chip 10 is formed of a pair of transparent flat plates 11 and 15 made of glass, quartz or the like. A sample drawing groove 12 and a migration groove 13 crossing each other at a crossing portion (hereinafter, called a crossing portion 14) are formed in an upper surface of the lower transparent flat plate 11 (refer to FIG. 8(b)). Through-holes 16 are provided in the upper transparent flat plate 15 at positions corresponding to the respective end portions of the grooves 12 and 13 (refer to FIG. 8(a)). The grooves 12 and 13 are provided in the surface of the transparent flat plate 11, for example, by etching, and a width of the groove portions is about 10–100 µm and a depth thereof is about 5–50 µm.

As shown in FIG. 8(c), a pair of the transparent flat plates 11 and 15 is bonded together so that the grooves 12 and 13 are positioned inside the flat plates 11 and 15. Accordingly, a sample introducing flow path 17 communicating with outside through the first and second reservoirs R1 and R2 formed by the through-holes 16 and a separating flow path 18 communicating with outside through the third and fourth reservoirs R3 and R4 are formed in the electrophoretic chip 10. The respective reservoirs R1 to R4 receive capillaries therein for introducing a liquid, such as a migration liquid, from outside. Electrodes (not shown) for applying a voltage to a migration liquid reserved in the reservoirs are provided, respectively. The electrode is formed of, for example, a conductive thin film formed by photolithography on the surface of one of the transparent flat plates, and extends to the end surface of the transparent flat plate.

A general procedure of measurement using such an electrophoretic chip 10 is as follows. First, the whole flow paths are filled with the migration liquid. Then, the first reservoir R1 is filled with a small amount (about 1–2 µl) of the sample solution, and a high voltage where a flow design and a migration condition are optimized is applied to the respective reservoirs R1 to R4. As an example, a voltage of 0.6 kV is applied to the first and fourth reservoirs R1 and R4; a voltage of 0.3 kV is applied to the third reservoir R3; and the second reservoir R2 is grounded. Then, the sample injected into the first reservoir R1 flows into the sample introducing flow path 17 due to an electric potential difference, passes through the crossing portion 14 and moves toward the second reservoir R2. At this time, the migration liquid also moves toward the second reservoir R2 from the third and fourth reservoirs R3 and R4, respectively, so that the sample does not diffuse to the separating flow path 18 during the sample introducing period.

Then, a voltage of 0.2 kV is applied to the first and second reservoirs R1 and R2; a voltage of 0.5 kV is applied to the third reservoir R3; and the fourth reservoir R4 is grounded. Accordingly, the sample present at the crossing portion 14 is introduced into the separating flow path 18 due to an electric potential difference, and migrates toward the fourth reservoir R4. In the sample introducing flow path 17, the sample present on a side of the first reservoir R1 from the crossing portion 14 moves back to the first reservoir R1; and the sample present on a side of the second reservoir R2 from the crossing portion 14 moves back to the second reservoir R2. Therefore, only the sample in a predetermined quantity according to a volume of the crossing portion 14 is introduced into the separating flow path 18.

As described (above, when the sample migrates in the separating flow path 18, the respective components contained in the sample are separated. With respect to the sample separated as described above, an electroferrogram, where an abscissa axis represents a migration time, is obtained through one point UV absorption detection using an ultraviolet visible absorption detector or through one point fluorescence detection using a fluorescence detector having an incident-light fluorescence optical system.

When the sample is detected at just one point on the separating flow path 18, it is difficult to obtain a whole image of the sample components separating and moving along the separating flow path 18. In the UV absorption detection using the ultraviolet visible absorption detector as disclosed in Japanese Patent No. 3077609, it is possible to obtain an image of the sample components spreading in a predetermined area along the separating flow path 18. However, the sensitivity of the UV detection using light absorption of the sample itself is inferior to that of the fluorescent detection. Accordingly, it is difficult to detect a component having a low concentration or low light absorption. The fluorescent detection is not greatly affected by background light as compared with the UV detection. However, it is necessary to reduce the effect of the background light for further improving the accuracy and the sensitivity.

In view of the above problems, an object of the invention is to provide a component analyzing apparatus using a component analyzing microchip for separating sample components through an electrophoretic migration, a liquid-supply pump or the like, wherein the separated sample components are detected over a predetermined area along a flow path at a high sensitivity, not at one point on the separating flow path of the microchip.

Further objects and advantages of the invention will be apparent from the following description of the invention.

SUMMARY OF THE INVENTION

In order to attain the above objects, the present inventor has developed an apparatus for detecting fluorescence and scattered light emitted from a sample component labeled with fluorescence present in the separating flow path by using a proximity field light employed in a total reflection fluorescence microscope or the like as an exciting light.

According to a first aspect of the present invention, a component analyzing apparatus includes:

a) a microchip having a fine separating flow path for separating components when a sample solution labeled with fluorescence passes through;

b) a light irradiation device for irradiating light to a predetermined area of the microchip at a predetermined angle so that the proximity field light irradiates at least a portion of the separating flow path of the microchip; and c) a light detecting device for receiving the fluorescence discharged from the sample solution labeled with fluorescence present in the separating flow path with the proximity field light generated from light irradiated by the light irradiating device as excitation light.

According to a second aspect of the present invention, a component analyzing apparatus includes:

a) a microchip having a fine separating flow path for separating components when a sample solution labeled with fluorescence passes through, and a light guide for irradiating at least a portion of the separating flow path with the proximity field light;

(b) a light irradiating device for irradiating light so that light is introduced into the light guide to cause a total reflection at an interface of the light guide of the microchip; and (c) a light detecting device for receiving the fluorescence discharged from the sample solution present in the separating flow path with the proximity field light generated on an outer side of the interface of the light guide as excitation light.

In the component analyzing apparatus according to the first aspect, the sample components in the sample solution are labeled with fluorescence in a suitable method, and flow through the separating flow path to be separated. A part or the whole portion of the sample components labeled with fluorescence in the separating flow path is excited by the proximity field light to thereby discharge the fluorescence, and the light detecting device detects the fluorescence. In order to generate the proximity field light, in the component analyzing apparatus, the light irradiating device irradiates light to a predetermined area of the micro-chip at a predetermined angle. Light transmits the transparent base member, such as glass and quartz, of the micro-chip, and reaches the separating flow path. Then, light enters the separating flow path with an angle larger than a critical angle relative to the interface between the sample solution filled in the separating flow path and the base member, and causes the total reflection. At this time, the proximity field light leaks on the other side of the interface, i.e. in the sample solution.

In the component analyzing apparatus according to the second aspect, in order to generate the proximity field light, the micro-chip is provided with the light guide having a refractive index at least higher than that of the base member, such as glass and quartz. The light irradiating device introduces light to the light guide, and light proceeds while being totally reflected. At this time, the proximity field light leaks on the other side of the interface, i.e. in an interior of the base member of the micro-chip, and transmits through the interior of the base member to reach the separating flow path.

In any case, since the proximity field light is locally generated only in the vicinity of a place where light is totally reflected, it is possible to reduce an influence of background light on detecting the fluorescence and scattered light from the sample solution. As a result, it is possible to detect light from the sample solution at an extremely high ratio of S/N to thereby attain high sensitivity and accuracy.

Also, light is irradiated to an adequately determined area and the light guide is formed at an adequately designed position. Accordingly, it is possible to generate the proximity field light not only at one point in the separating flow path but also at a portion or the whole portion thereof, so that the fluorescent substance of the sample solution in the flow path is excited. Therefore, it is possible to perform not only one-point detection, but also obtain an image of the sample moving over a wide range along the separating flow path. Further, the image is detected by the fluorescence, thereby obtaining high sensitivity as compared with the UV image detection. It is suitable to accurately obtain a separating condition of the sample at a real time.

DETAILED DESCRIPTION OF PREFERRED EMBODIMENTS

Hereunder, embodiments of the present invention will be explained with reference to the accompanying drawings. A component analyzing apparatus according to a first embodiment of the present invention will be described with reference to FIGS. 1 to 5.

Figure 1:
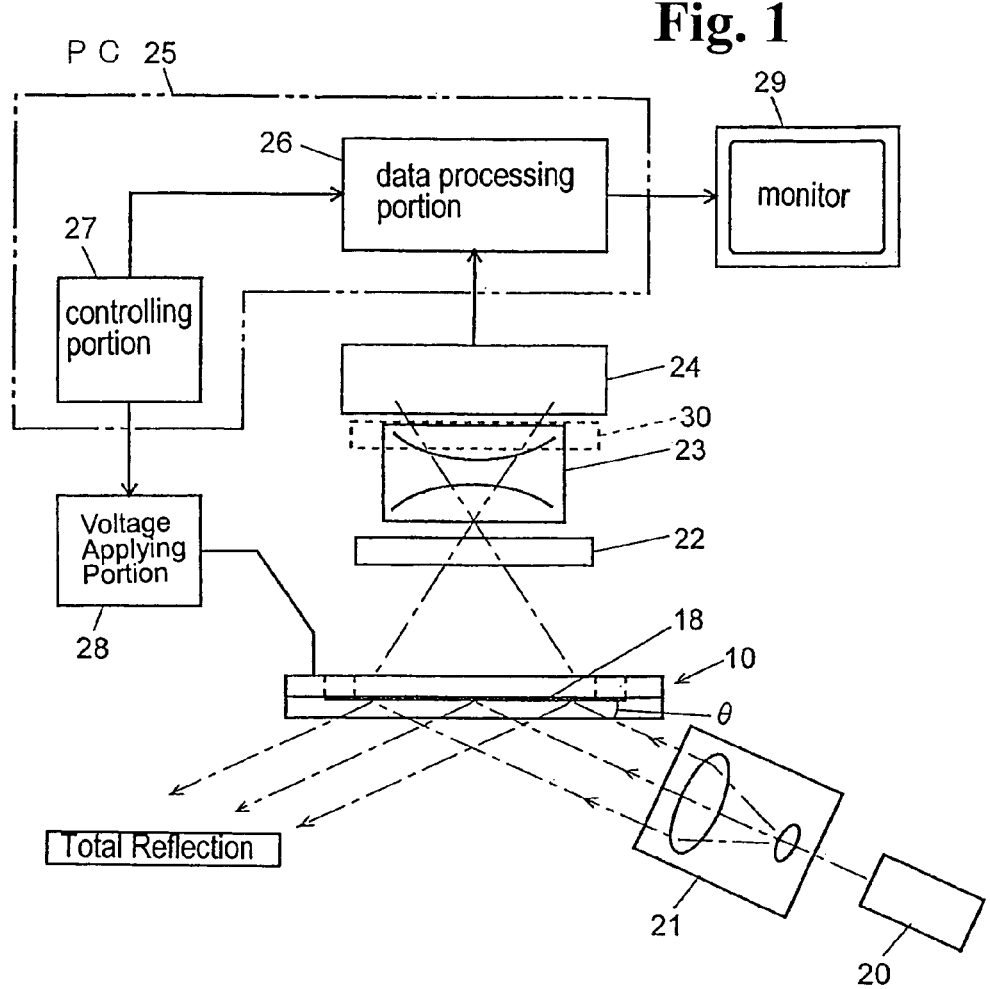
FIG. 1 is a block diagram showing an essential part of a component analyzing apparatus according to a first embodiment of the present invention.
Figure 2:
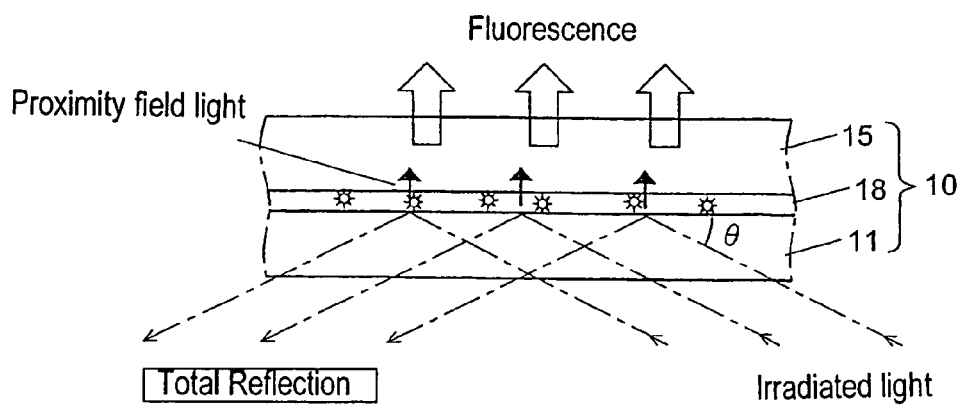
FIG. 2 is a sectional view of an electrophoretic chip of the component analyzing apparatus in the first embodiment.

FIG. 1 is a block diagram of an essential part of the component analyzing apparatus, and FIG. 2 is a sectional view of an electrophoretic chip 10. The electrophoretic chip 10 may have a conventional structure described above. The present apparatus detects fluorescence, and a sample to be analyzed is labeled with fluorescence with an appropriate device beforehand. Specifically, for example, when the component to be analyzed is dsDNA, an intercalator, fluorescent plasma, a substance labeled with fluorescence and the like can be used.

In FIG. 1, a voltage applying portion 28 consecutively applies a high voltage to reservoirs $R_1$ to $R_4$ of the electrophoretic chip 10 according to an instruction from a controlling portion 27 in a personal computer (PC) 25. An exciting laser beam source 20 and a beam expander 21 as a light irradiating device are disposed below the electrophoretic chip 10. The laser beam source 20 irradiates laser beam through an area suitably adjusted by the beam expander 21 to a predetermined area on a lower surface of the electrophoretic chip 10. The irradiated beam enters an interior of the transparent flat plate 11 and reaches the separation flow path 18 filled with a sample solution. At this time, the light irradiating device is arranged so that the irradiated light enters with a total reflection angle larger than a critical angle $\theta c$ relative to an interface between the transparent flat plate 11 and the sample solution in the separating flow path 18.

Generally, the critical angle θc is obtained by the following equation:

$$\sin \theta c = n2/n1,$$

where n1 is a refractive index of a substance (in the present embodiment, the transparent flat plate 11) on one side of a reflection surface; n2 represents a refractive index of a substance (in the present embodiment, the sample solution) on the other side of the reflection surface. For example, when the transparent flat plate 11 is formed of glass (n=1.52) and the sample solution is water (n=1.33), the critical angle θc is about 61°. Incidentally, when light enters the transparent flat plate 11 from the atmosphere or vacuum, light reflects. Accordingly, the light irradiating device is arranged taking the refraction into consideration so that the total reflection condition is satisfied.

Under the total reflection condition, as shown in FIG. 2, the irradiated light is totally reflected at the interface between the transparent flat plate 11 and the sample solution in the separating flow path 18. At this time, light called "proximity field light" leaks on the other side of the reflecting surface, i.e. the inner side of the sample solution. Since the sample components contained in the sample solution are labeled with fluorescence, the proximity field light excites the fluorescent solution to thereby discharge spontaneous fluorescence. The fluorescence is introduced into a CCD sensor 24 as a light detecting device through a wavelength filter 22 and an objective lens 23. The wavelength filter 22 selects only a target wavelength of the fluorescence. A receipt signal obtained at the CCD sensor 24 is inputted into a data processing portion 26, and a process, such as an image processing, is carried out under control of the controlling portion 27 to display a two dimensional image on a monitor 29.

Figure 3:
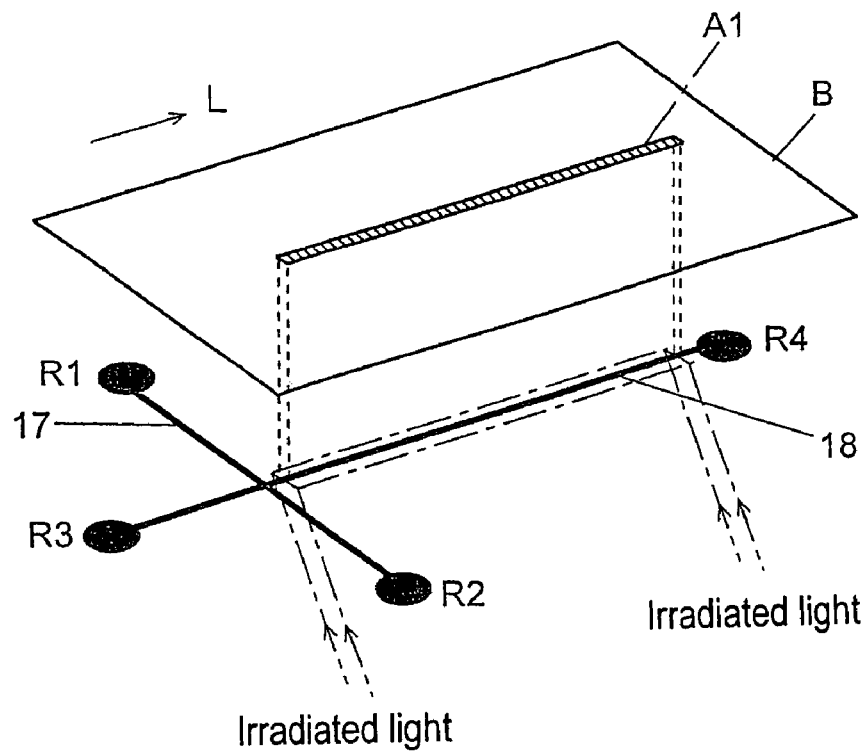
FIG. 3 is a schematic view showing a measuring method of the component analyzing apparatus in the first embodiment.
Figure 4:
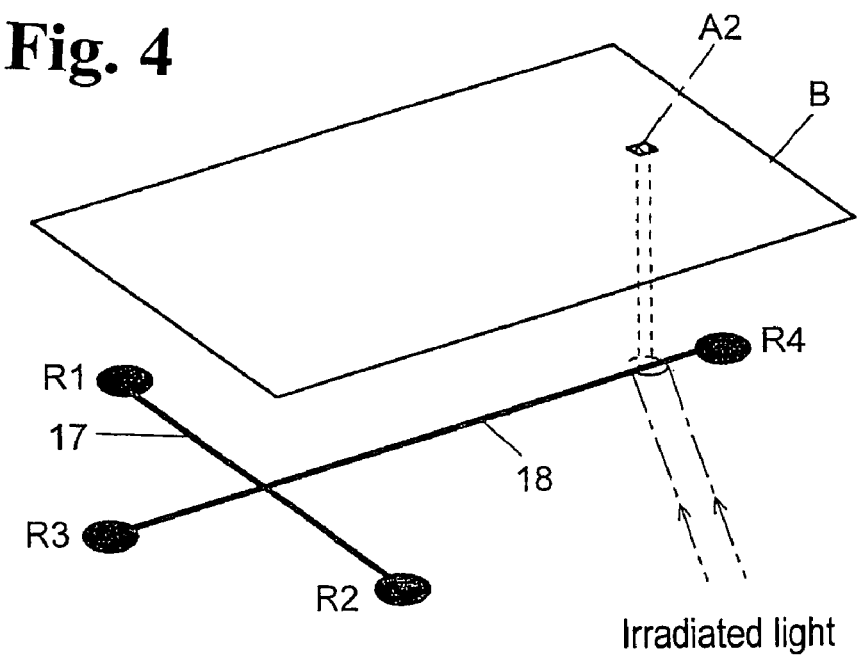
FIG. 4 is a schematic view showing a measuring method of the component analyzing apparatus in the first embodiment.
Figure 5:
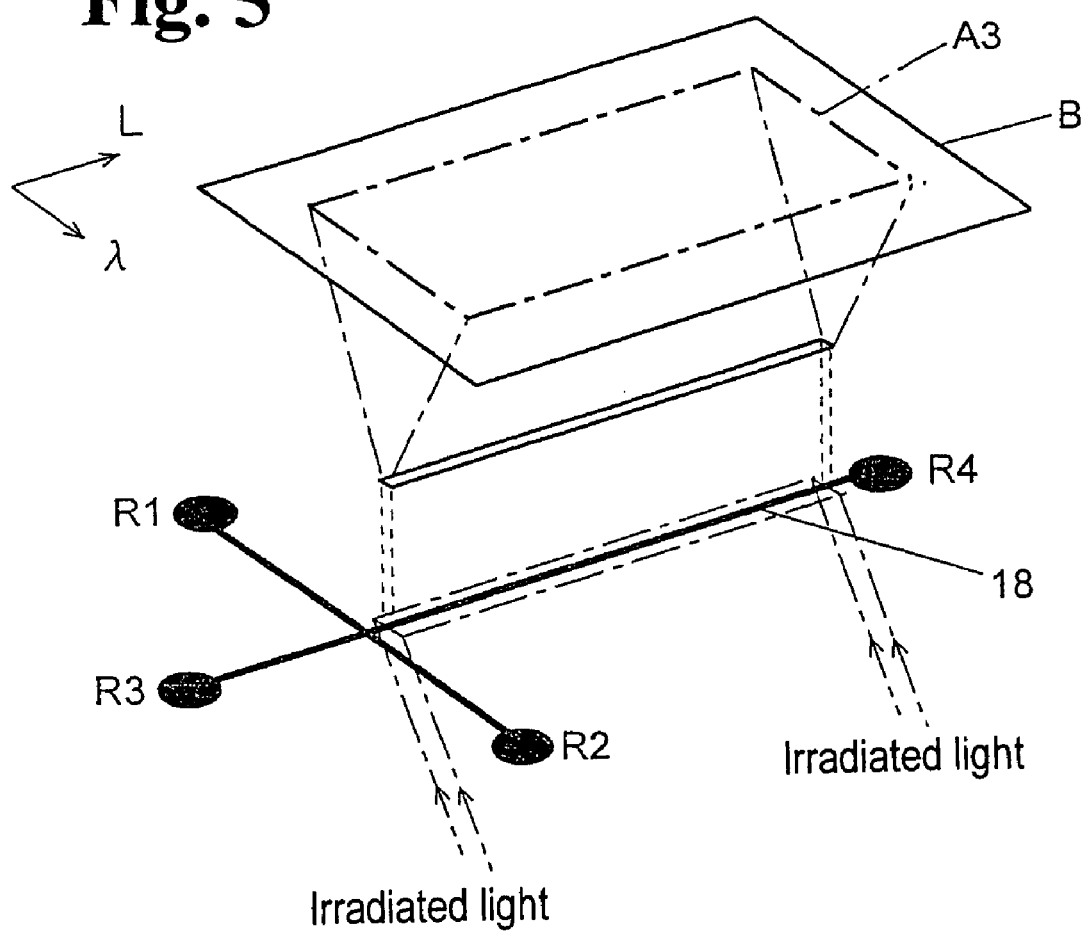
FIG. 5 is a schematic view showing a measuring method of the component analyzing apparatus in the first embodiment.

Since the proximity field light exists only at a place very close to a position where light is irradiated, it is possible to determine an area of the fluorescent image due to the sample components in the separating flow path 18 according to the area where light is irradiated. FIGS. 3 to 5 are schematic views showing various measuring methods.

FIG. 3 shows a case where the imaging is carried out at a predetermined area (a portion or the whole portion of the separating flow path 18) along the separating flow path 18 to obtain information relating to conditions of separation and movement of the components in the separating flow path 18. A linear fluorescent image A1 along an extending direction of the separating flow path 18 appears on a two dimensional image B obtained at the CCD sensor 24. A separating process is momentarily changing, and can be monitored in real time or time closer thereto by processing the signal obtained at the CCD sensor 24 at a predetermined time interval. Incidentally, in order to obtain the fluorescent image A1, the CCD image sensor is not necessarily used as the light detecting device. A CCD linear sensor, linear PDA (photo-diode array) detector or the like may be used.

FIG. 4 shows a case where one point of a certain position in the separating flow path 18 is detected. On the two dimensional image B obtained at the CCD sensor 24, a fluorescent spot A2 corresponding to the detected point on the separating flow path 18 appears. In the data processing portion 26, by processing the fluorescent intensity of the fluorescent spot A2 obtained at a predetermined time interval, it is possible to form an electroferrogram. Incidentally, when only one point is detected, the CCD image sensor is not necessarily used as the light detecting device. A photo-electron multiplier, a photo-diode detector, an avalanche photo-diode detector or the like may be used.

FIG. 5 shows a case where an image of spectroscopy is obtained at a predetermined area along the separating flow path 18 in order to obtain more detailed information with respect to the separation and movement of the components in the separating flow path 18. In this case, in FIG. 1, a transmission type wavelength dispersion element 30 is installed in front of the CCD sensor 24 instead of the wavelength filter 22. The wavelength dispersion element 30 has a function for dispersing a wavelength in a direction substantially perpendicular to the extending direction of the separating flow path 18. On the two dimensional image B obtained at the CCD sensor 24, a two dimensional spectroscopic image A3 having positional information along the extending direction of the separating flow path 18 in the L axis direction and wavelength information of the fluorescence in the λ axis direction perpendicular to the L direction. Accordingly, by using a plurality of the fluorescent substances having different emission wavelengths, it is possible to obtain detailed moving and separating states of the plural components.

In the component analyzing apparatus of the first embodiment, as described above, the electrophoretic chip 10 may have the conventional structure. On the contrary, in a component analyzing apparatus according to a second embodiment of the invention, the electrophoretic chip 10 has a modified structure so that the proximity field light is generated by a method different from that of the first embodiment to excite the fluorescent substance of the sample components in the separating flow path 18.

Figure 6:
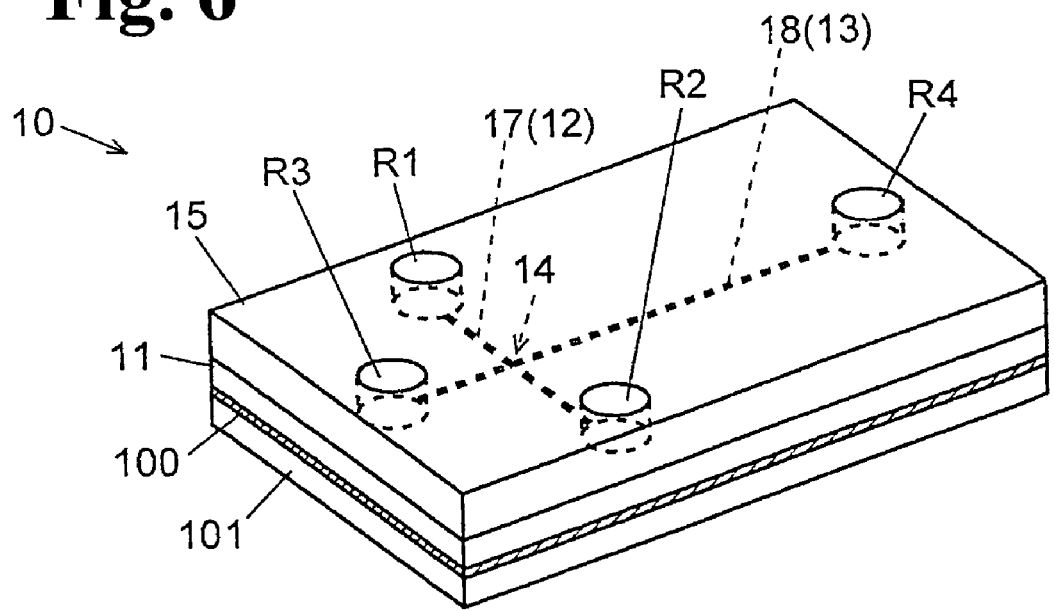
FIG. 6 is a perspective view showing an electrophoretic chip of a component analyzing apparatus according to a second embodiment of the present invention.
Figure 7:
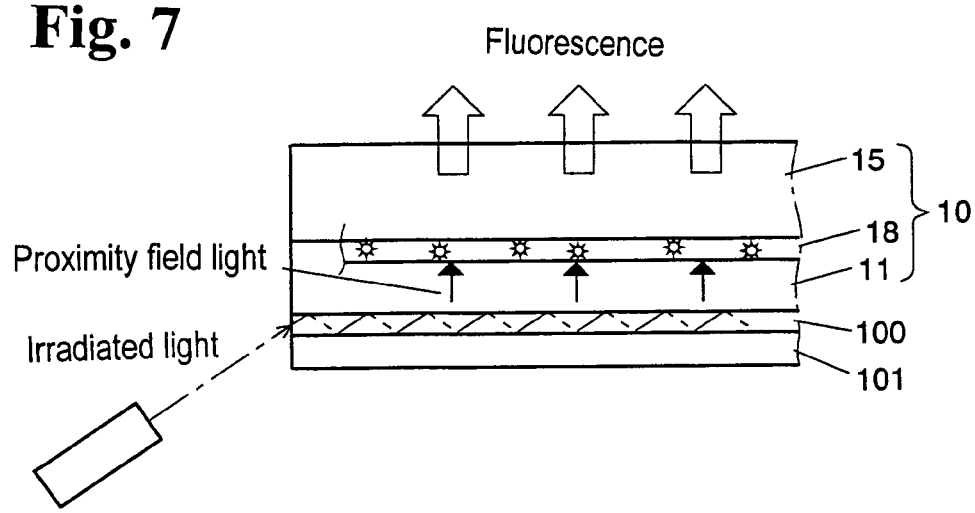
FIG. 7 is a sectional view of an electrophoretic chip of the component analyzing apparatus in the second embodiment.
Figure 8A:
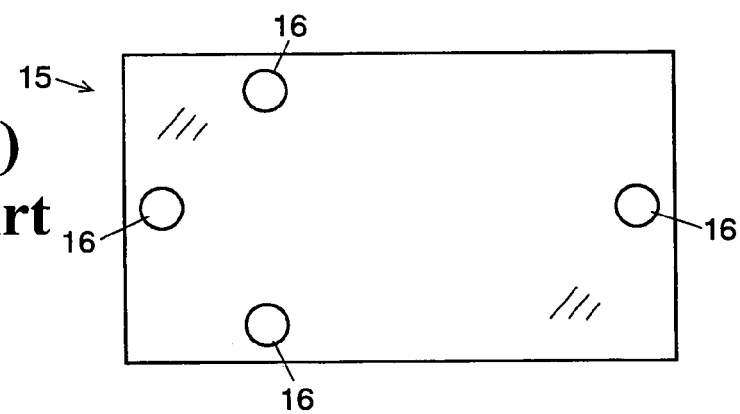
FIGS. 8(a)–8(c) are views showing a conventional electrophoretic chip.
Figure 8B:
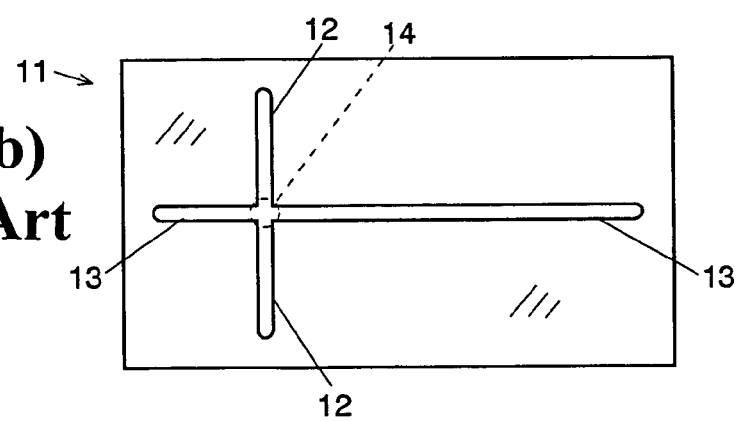
Figure 8C:
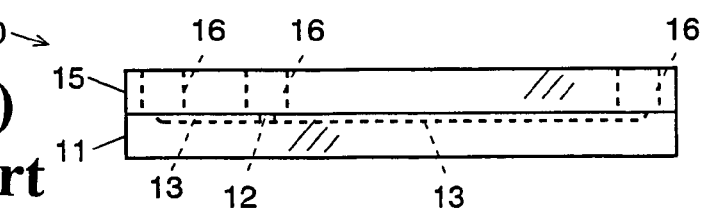
Figure 9:
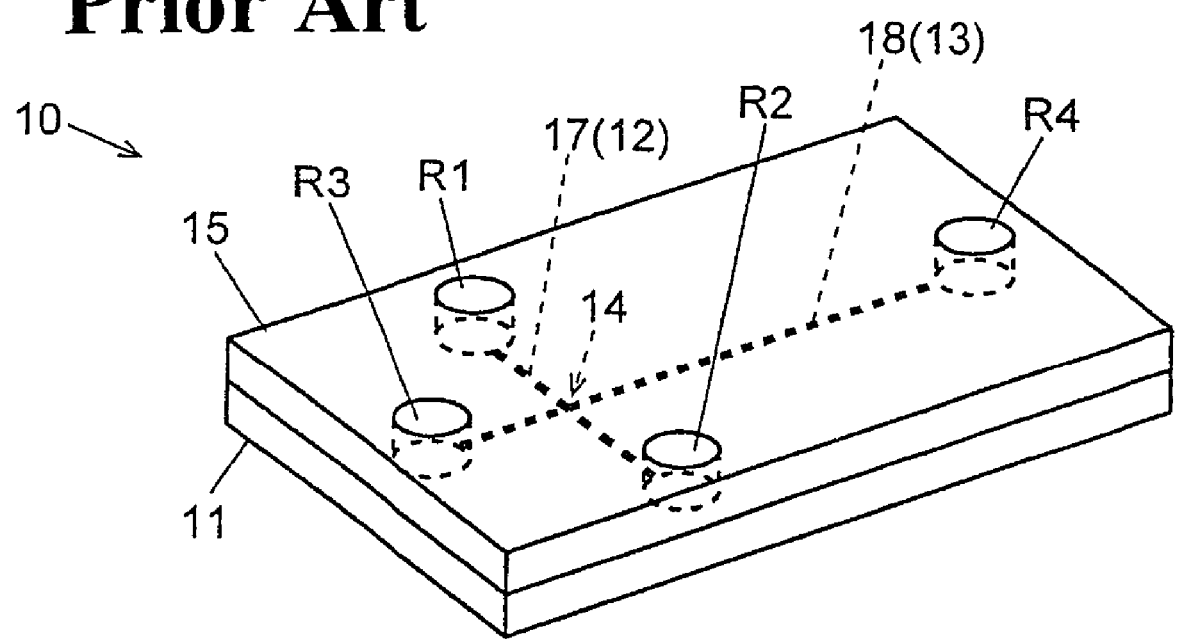
FIG. 9 is a perspective view of the conventional electrophoretic chip.

FIG. 6 is a perspective view showing the electrophoretic chip 10 of the component analyzing apparatus according to the second embodiment, and FIG. 7 is a sectional view of the electrophoretic chip 10 in a state that fluorescence is generated. In the electrophoretic chip 10, a light guide layer 100 formed of a thin film with a thickness of, for example, an order of 200 to 500 μm, is laminated on the lower surface of the transparent flat plate 11. A flat plate 101 formed of a material having a refractive index same or approximately same as that of the transparent flat plate 11 is attached to the lower surface of the light guide layer 100. More specifically, the light guide layer 100 is sandwiched between the transparent flat plate 11 and the flat plate 101.

It is necessary that the light guide layer 100 is formed of a material having a refractive index higher than those of the transparent flat plate 11 and the flat plate 101. Preferably, the material of the light guide layer 100 has a refractive index as high as possible. For example, it is preferable to use tantalum pentoxide ($Ta_2O_5$) having a refractive index of about 2.1 at the vicinity of a wavelength of 550 nm; or cerium oxide ($CeO_2$) having a refractive index of about 2.2 at the vicinity of a wavelength of 550 nm.

As shown in FIG. 7, light is guided into the end portion of the light guide layer 100 at a predetermined angle from the light irradiating device including the laser beam source 20 as described above or the like. The incident angle of light is determined such that light enters at the total reflection angle larger than the critical angle θc relative to the interfaces between the light guide layer 100 and the transparent flat plate 11 and the flat plate 101, so that light proceeds in the light guide layer 100 while repeating the total reflection at the interfaces. When light is totally reflected, the proximity field light leaks on the upper side of the interface between the light guide layer 100 and the transparent flat plate 11.

At this time, the intensity of the proximity field light becomes weaker as moving away from the interface. However, when the transparent flat plate 11 has a sufficiently thin thickness, even at a point where the proximity field light reaches the separating flow path 18, the proximity field light has the intensity sufficiently strong to excite the fluorescent substance bonded with the sample components in the separating flow path. Accordingly, the fluorescence is generated from the sample solution to obtain various fluorescent images as in the first embodiment.

As the refractive index of the light guide layer 100 increases, the critical angle θc decreases, so that the total reflection angle can be made small. When the total reflection angle is small, the total reflection occurs at a higher frequency. As described above, the proximity field light is generated only at a place very close to the interface where light is totally reflected. Accordingly, as the frequency or repeating density of the total reflection increases, the proximity field light has higher intensity. Further, the repeating density becomes uniform, so that the fluorescent substance is excited uniformly.

Incidentally, it is not necessary to provide the light guide layer 100 along the whole lower surface of the transparent flat plate 11. It is sufficient that the light guide layer 100 is provided at the lower surface of the separating flow path 18 where at least the fluorescent image is desired to form. Also, since the proximity field light reaching the separating flow path 18 becomes weak when a thickness of the transparent flat plate 11 is thick, it is desirable that the transparent flat plate 11 has a thin thickness as little as possible.

The above-described embodiments are only an example according to the present invention, and appropriate modifications, adjustments, additions or the like can be made within the scope of the present invention. For example, in the above embodiments, the sample solution flows in the microchip through the electrophoretic migration. In the present invention, it is possible to use a liquid-supply pump or utilize a pressure difference at both ends of a flow path to flow the sample solution. In other words, the method for separating the components in the microchip and procedures thereof are not limited especially.

The disclosure of Japanese Patent Application No. 2003-284633 filed on Aug. 1, 2003 is incorporated in the application.

While the invention has been explained with reference to the specific embodiments of the invention, the explanation is illustrative and the invention is limited only by the appended claims.

What is claimed is:

1. A component analyzing apparatus for analyzing a component labeled with fluorescence in a sample, comprising:
    a microchip having a fine separating flow path for separating the component when the sample flows through the flow path,
    a light irradiation device disposed adjacent to the microchip for irradiating light to a predetermined area of the microchip at a predetermined angle so that proximity field light is irradiated to at least a portion of the separating flow path of the microchip, and
    a light detecting device disposed adjacent to the microchip for detecting fluorescence discharged from the sample in the separating flow path with the proximity field light as excitation light.

2. A component analyzing apparatus according to claim 1, wherein said microchip further includes a light guide for irradiating the proximity field light to at least a portion of the separating flow path, said light irradiating device introducing light to the light guide to cause a total reflection at an interface of the light guide so that said light detecting device detects the fluorescence with the proximity field light generated on an outer side of the interface as the excitation light.

3. A component analyzing apparatus according to claim 2, wherein said light guide is formed of a material having a refractive index higher than that of a material of the microchip.

4. A component analyzing apparatus according to claim 1, wherein said light irradiation device includes an exciting laser beam source for irradiating the light, and a beam expander for receiving laser beam as the light so that the laser beam passing through the beam expander is irradiated to an entire area of the separating flow path to cause a total reflection at an interface of the separating flow path.

5. A component analyzing apparatus according to claim 4, wherein said light detecting device includes a sensor, and a wavelength filter or a wavelength dispersion element for providing detected light to the sensor.

6. A component analyzing apparatus according to claim 5, wherein said microchip is formed of transparent flat plates bonded together, at least one of the flat plates having a groove inside the flat plates to form the flow path.

* * * * *